United States Patent
O'Heeron et al.

(10) Patent No.: US 12,090,174 B2
(45) Date of Patent: Sep. 17, 2024

(54) FIBROBLAST THERAPY FOR TREATMENT OF DUCHENNE MUSCULAR DYSTROPHY

(71) Applicant: SPINALCYTE, LLC, Houston, TX (US)

(72) Inventors: Pete O'Heeron, Houston, TX (US); Thomas Ichim, San Diego, CA (US)

(73) Assignee: SPINALCYTE, LLC, Houston, TX (US)

( * ) Notice: Subject to any disclaimer, the term of this patent is extended or adjusted under 35 U.S.C. 154(b) by 878 days.

(21) Appl. No.: 16/887,971

(22) Filed: May 29, 2020

(65) Prior Publication Data

US 2020/0376042 A1    Dec. 3, 2020

Related U.S. Application Data

(60) Provisional application No. 62/855,014, filed on May 31, 2019.

(51) Int. Cl.
| | |
|---|---|
| *A61K 35/33* | (2015.01) |
| *A61K 9/00* | (2006.01) |
| *A61K 35/17* | (2015.01) |
| *C12N 5/077* | (2010.01) |

(52) U.S. Cl.
CPC ............ *A61K 35/33* (2013.01); *A61K 35/17* (2013.01); *C12N 5/0656* (2013.01); *A61K 9/0019* (2013.01); *C12N 2502/1114* (2013.01)

(58) Field of Classification Search
None
See application file for complete search history.

(56) References Cited

U.S. PATENT DOCUMENTS

| | | | |
|---|---|---|---|
| 2003/0059414 A1* | 3/2003 | Ho | A61P 25/02 435/368 |
| 2004/0043008 A1 | 3/2004 | Vilquin et al. | |
| 2014/0112898 A1 | 4/2014 | Mathis et al. | |
| 2014/0287495 A1 | 9/2014 | Mummery | |
| 2017/0304370 A1* | 10/2017 | Lukasiewicz Hagai | C12N 5/0671 |

FOREIGN PATENT DOCUMENTS

| | | |
|---|---|---|
| WO | 1996/09373 A1 | 3/1996 |
| WO | WO 2018/124292 | 7/2018 |
| WO | 2020/146874 A1 | 7/2020 |

OTHER PUBLICATIONS

Gibson et al. J Cell Science 108:207-214 (1995) (Year: 1995).*
Mamidi et al., J Cell Biochem. May 2011;112(5):1353-1363 (Year: 2011).*
Denu et al., Acta Haematol. 2016;136:85-97 (Year: 2016).*
Kharraz et al. "Understanding the Process of Fibrosis in Duchenne Muscular Dystrophy", BioMed Research International, Mar./May 2014, vol. 2014, p. 1-11.
Extended European Search Report issued in European Patent Application No. 20813779.4, dated Jun. 15, 2023.
Ichim et al., "Fibroblasts as a practical alternative to mesenchymal stem cells," Journal of Translational Medicine, 16(212), pp. 1-9, 2018.
Alt et al., "Fibroblasts share mesenchymal phenotypes with stem cells, but lack their differentiation and colony-forming potential," Biol. Cell., 103:197-208, 2011.
Balducci et al., "The differences between mesenchymal stromal cells and fibroblasts," In: The Biology and Therapeutic Application of Mesenchymal Cells, First Edition, John Wiley & Sons, Chapter 30, pp. 441-455, 2017.

* cited by examiner

*Primary Examiner* — Daniel C Gamett
(74) *Attorney, Agent, or Firm* — Norton Rose Fulbright US LLP

(57) ABSTRACT

Disclosed are compositions and methods of treating muscular dystrophies, including Duchenne Muscular Dystrophy (DMD) through administration of fibroblasts and modified fibroblasts systemically and locally. In certain embodiments, fibroblast cells are utilized for replacement of dystrophin through fusion and/or other means of horizontal gene transfer. In other embodiments, the disclosure teaches the use of fibroblasts for reduction of inflammatory reactions and/or immunological reactions which propagate and enhance myodestructive aspects of Duchenne Muscular Dystrophy. In other embodiments, fibroblasts are utilized as vectors for gene therapy and/or gene modifications approaches.

23 Claims, No Drawings

FIBROBLAST THERAPY FOR TREATMENT OF DUCHENNE MUSCULAR DYSTROPHY

CROSS-REFERENCE TO RELATED APPLICATIONS

This application claims priority to U.S. Provisional Patent Application Ser. No. 62/855,014, filed May 31, 2019, which is incorporated by reference herein in its entirety.

TECHNICAL FIELD

Embodiments of the disclosure include at least the fields of cell biology, molecular biology, neurobiology, and medicine.

BACKGROUND

Maintenance and repair of skeletal muscle tissue is essential for survival of locomotor organisms. For example, muscle strains or tears can happen when a muscle is stretched beyond its limit or if there is a direct blow to a muscle, tearing the muscle fibers. Muscle injury frequently occurs near the point where the muscle joins the tough, fibrous connective tissue of the tendon [1]. Muscle injuries are common and range from where only a few muscle fibers are stretched or torn, to more severe tears with muscle pain and tenderness, mild swelling, noticeable loss of strength and sometimes bruising, to muscle tears that rip the muscle into two separate pieces or cause the fleshy part of the muscle to break away from the tendon, resulting in complete loss of muscle function, considerable pain, swelling, tenderness and discoloration [2]. During aging, much of the muscle mass is lost. In addition, fiber-type changes occur and increased fat deposition in muscle occurs. Loss of mass and these other changes can have a significant impact on the ability of an individual to continue to perform certain daily activities, as well as participate in more strenuous activities, possible earlier in life [3-7].

Dystrophin-associated muscular dystrophies range from the severe Duchenne muscular dystrophy (DMD), which is the most common muscular dystrophy, to the milder Becker muscular dystrophy (BMD) [8, 9]. Mapping and molecular genetic studies indicate that both types of muscular dystrophy are the result of mutations in the dystrophin gene. Duchenne muscular dystrophy eventually affects all voluntary muscles, as well as heart and breathing muscles. Survival is rare beyond the early 30's, and death typically occurs from respiratory failure (suffocation) or heart disorders. DMD is characterized by mutations in the dystrophin gene that result in a loss of the dystrophin protein. Loss of dystrophin causes an associated reduction in proteins of the dystrophin glycoprotein complex (DGC) [10], leading to contraction-induced sarcolemmal weakening [11, 12], muscle tearing [13], fibrotic infiltration and rounds of degeneration and failed regeneration affecting satellite cell populations [14].

Muscle tissue possesses regenerative cells, in some cases the major regenerative cells are satellite cells, which lie juxtaposed to the myofiber and underneath the basal lamina, are a source of new myonuclei required for skeletal muscle growth, repair and regeneration [15]. In uninjured skeletal muscle, the majority of these cells are mitotically quiescent, exhibit a high nuclear to cytoplasmic volume and do not express members of the MyoD family of transcription factors [16]. Subsequent to muscle injury satellite cells acquire an activated phenotype with the cells rapidly increasing their cytoplasmic volume, egressing from the basal lamina and proliferating prior to their fusion into existing, damaged myofibers or with each other to form new myofibers [17]. While the majority of satellite cells divide only once or twice prior to fusion and a subpopulation of satellite cells appears to possess an "early" stem cell phenotype based on their failure to fuse and fail to incorporate DNA label over 14 days.

Another aspect DMD is the fundamental role of inflammation and immunopathology. One indication of the potent role of inflammation in progression of DMD is seen by the fact that anti-inflammatory steroids have been shown to delay disease progression [18]. Other support for the immunological/inflammatory pathogenesis of DMD comes from studies showing involvement of a variety of immune cells. For example, in one study, infiltrating myeloid cells were shown to cluster in damaged areas of dystrophic skeletal muscles. These cells where shown to produce the natural ligand of mineralocorticoid receptor (MR), aldosterone, which causes muscle damage [19]. Macrophages of the M1 lineage appear to promote progression of muscle damage whereas M2 seem to promote regeneration. One published study illustrating this point examined mechanisms by which macrophages promote musclar dystrophy and assess whether the phenotype of the macrophages changes between the stage of peak muscle necrosis (4 weeks of age) and muscle regeneration (12 weeks). It was found that in 4-week-old mdx mice, muscles contain a population of pro-inflammatory, classically activated M1 macrophages that lyse muscle in vitro by nitric oxide-mediated mechanisms. The importance of nitric oxide in muscle pathology was demonstrated by genetic ablation of the iNOS gene. This resulted in significant reduction in muscle membrane lysis in 4-week-old mdx mice in vivo. It was also found that, 4-week mdx muscles also contain a population of alternatively activated, M2a macrophages that express arginase. In vitro assays show that M2a macrophages reduce lysis of muscle cells by M1 macrophages through the competition of arginase in M2a cells with iNOS in M1 cells for their common, enzymatic substrate, arginine. During the transition from the acute peak of mdx pathology to the regenerative stage, expression of IL-4 and IL-10 increases, either of which can deactivate the M1 phenotype and promote activation of a CD163+, M2c phenotype that can increase tissue repair. These findings support that IL-10 stimulation of macrophages activates their ability to promote satellite cell proliferation. Deactivation of the M1 phenotype is also associated with a reduced expression of iNOS, IL-6, MCP-1 and IP-10 [20]. Supporting the protective role of M2 macrophages is another study in which ablation of IL-10 expression in mdx mice was shown to increased muscle damage and reduce mouse strength. Treating mdx muscle macrophages with IL-10 reduced activation of the M1 phenotype, assessed by iNOS expression, and macrophages from IL-10 null mutant mice were more cytolytic than macrophages isolated from wild-type mice. These data also showed that muscle cells in mdx muscle expressed the IL-10 receptor, suggesting that IL-10 could have direct effects on muscle cells [21].

In the clinical context, as a consequence of the DGC inefficiency is the enhanced rate of myofibre damage and subsequent death during muscle contraction. Although satellite cells compensate for muscle fiber loss in the early stages of disease [22], eventually these progenitors become exhausted as witnessed by shorter telomere length and inability to generate new muscle [23]. In the MDX mouse model of DMD, embryonic loss of myocyte progenitors has been described, thus further predisposing for poor compensatory myogenesis [24]. As a result of high demands for myogenesis and poor compensatory mechanisms, fibrous and fatty connective tissue eventually overtake the functional myofibres both in animal models and in the clinical situation. Contributing to this process are inflammatory cell infiltration, cytokine production and complement activation [25, 26]. These changes culminate in progressive muscle wasting, with majority of patients being wheelchair-bound in their early teens. Patients succumb to cardiac/respiratory failure in their twenties, although rare cases of survival into the thirties has been reported [27].

With exception of corticosteroids, which have limited activity and cause numerous adverse effects [28], therapeutic interventions in DMD have had little, if any success. Current areas of investigation include replacement gene therapy with dystrophin [29], induction of exon-skipping by antisense or siRNA to correct the open reading frame of mutated DMD genes [30], and transfer of myoblast or other putative progenitor cells [31-33]. Certain studies have been successful at restoration of dystrophin expression using allogeneic myoblasts under the cover of immune suppression, however significant functional benefits have not been reported [34-36]. Accordingly, there is a significant need in the art for new treatment approaches to Muscular Dystrophy.

BRIEF SUMMARY

The present disclosure is directed to compositions and methods for the treatment of one or more muscular dystrophies, including at least Duchenne muscular dystrophy, Becker muscular dystrophy, limb girdle, congenital, facioscapulohumeral, myotonic, Charcot-Marie-Tooth disease. myositis, polymyositis, dermatomyositis, oculopharyngeal, distal, and Emery-Dreifuss. In some embodiments, the muscular dystrophy is caused by or associated with a mutation in, or dysfunction of, the dystrophin gene. The muscular dystrophy may cause, or be associated, with symptoms including muscle deterioration, muscle weakness, abnormal locomotion, loss of muscle, flaccid muscles, shortening or muscles, fatigue, and/or cardiomyopathy. In some embodiments, the compositions and/or methods are used to reverse, ameliorate, or prevent one or more symptoms caused by, or associated with, the muscular dystrophy.

Certain embodiments encompass cellular compositions, or methods of use of compositions, that comprise adherent populations of cells. Adherent cells may be cells that stick to plastic, such as to a tissue culture plate. The populations of cells may be populations of fibroblasts and/or populations of endothelial cells. The fibroblasts may express CXCR-4. The population of cells, including population of fibroblasts, may be enriched for CXCR-4, such as (or such as about) 50%, 55%, 60%, 65%, 70%, 75%, 80%, 85%, 90%, 95%, 96%, 97%, 98%, 99%, or more of the population expressing CXCR-4, CD31, CD34, or any combination thereof. In addition or alternatively, <1%, <2%, <3%, <4%, <5%, <6%, <7%, <8%, <9%, or <10% of the population of cells may express CD14 and/or CD45. The fibroblasts may express markers selected from the group consisting of STRO-1, CD105, CD54, CD106, HLA-I markers, vimentin, ASMA, collagen-1, fibronectin, LFA-3, ICAM-1, PECAM-1, P-selectin, L-selectin, CD49b/CD29, CD49c/CD29, CD49d/CD29, CD61, CD18, CD29, thrombomodulin, telomerase, CD10, CD13, STRO-2, VCAM-1, CD146, and THY-1, and a combination thereof. The endothelial cells may express one or more markers selected from the group consisting of: a) extracellular vimentin; b) CD133; c) c-kit; d) VEGF receptor; e) activated protein C receptor; and f) a combination thereof. In some embodiments, the population of endothelial cells comprises endothelial progenitor cells.

The population of cells may be allogeneic, autologous, or xenogenic to an individual, including an individual being administered the population of cells. In some embodiments, the population of cells are matched by mixed lymphocyte reaction matching. Cells may be matched through mixed lymphocyte reaction matching by exposing the cells to a population of cells from a different individual and determining if there is an immune reaction between the two populations.

In some embodiments, the population of cells is derived from tissue selected from the group consisting of the placental body, placenta, adipose tissue, bone marrow, umbilical cord tissue, peripheral blood, hair follicle, cord blood, Wharton's Jelly, menstrual blood, endometrium, skin, omentum, amniotic fluid, and a combination thereof. In some embodiments, the population of cells, the population of fibroblasts, or the population of endothelial cells comprises human skin derived adherent cells. The human skin derived adherent cells may express a cyotkine selected from the group consisting of) FGF-1; b) FGF-2; c) HGF; d) interleukin-1 receptor antagonist; and e) a combination thereof. In some embodiments, the population of cells, the population of fibroblasts, or the population of endothelial cells express arginase, indoleamine 2,3 deoxygenase, interleukin-10, and/or interleukin 35. In some embodiments, the population of cells, the population of fibroblasts, or the population of endothelial cells express hTERT and Oct-4 but does not express a STRO-1 marker. In some embodiments, the population of cells, the population of fibroblasts, and/or the population of endothelial cells express STRO-1.

In some embodiments, the population of cells, the population of fibroblasts, or the population of endothelial cells has an ability to undergo cell division in less than 36 hours in a growth medium. In some embodiments, the population of cells, the population of fibroblasts, or the population of endothelial cells have an ability to proliferate at a rate of 0.9-1.2 doublings per 36 hours in growth media. In some embodiments, the population of cells, the population of fibroblasts, or the population of endothelial cells have an ability to proliferate at a rate of 0.9, 1.0, 1.1, or 1.2 doublings per 36 hours in growth media. The population of cells, population of fibroblasts, or population of endothelial cells may produce exosomes capable of inducing a 50% higher proliferation rate in human umbilical cord endothelial cells when cultured with the exosomes compared to human umbilical cord endothelial cells that have not been cultured with the exosomes. The induction of proliferation may occur when the exosomes are cultured with the human umbilical cord endothelial cells at a concentration of 10, 20, 30, 40, 50, 60, 70, 80, 90, 100, 110, 120, 130, 140, 150, 160, 170, 180, 190, 200, or more exosomes per cell.

In some embodiments, a population of cells, including a population of fibroblasts alone, are administered to an individual, including an individual having, or suspected of having, muscular dystrophy. The population of cells may be administered via any suitable route, including as non-limiting examples, intramuscularly and/or intravenously.

In some embodiments, a population of fibroblasts is optionally obtained, the population is then optionally contacted via culturing with a population of progenitor for T regulatory cells, wherein the culturing conditions may be suitable conditions for the generation of T regulatory cells, then the generated T regulatory cells are administered to an individual, including an individual with a muscular dystrophy. Culturing conditions that may be suitable conditions for the generation of T regulatory cells may comprise 1-100 IU/mL of IL-2 and/or 1 pg/mL-1 µg/mL of rapamycin. The cells may be exposed to the culturing conditions for at least one hour, at least one day, at least one week, at least one month, or at least 3 months.

The foregoing has outlined rather broadly the features and technical advantages of the present disclosure in order that the detailed description that follows may be better understood. Additional features and advantages will be described hereinafter which form the subject of the claims herein. It should be appreciated by those skilled in the art that the conception and specific embodiments disclosed may be readily utilized as a basis for modifying or designing other structures for carrying out the same purposes of the present designs. It should also be realized by those skilled in the art that such equivalent constructions do not depart from the spirit and scope as set forth in the appended claims.

DETAILED DESCRIPTION

I. Definitions

In keeping with long-standing patent law convention, the words "a" and "an" when used in the present specification in concert with the word comprising, including the claims, denote "one or more." Some embodiments of the disclosure may consist of or consist essentially of one or more elements, method steps, and/or methods of the disclosure. It is contemplated that any method or composition described herein can be implemented with respect to any other method or composition described herein and that different embodiments may be combined.

As used herein, the terms "or" and "and/or" are utilized to describe multiple components in combination or exclusive of one another. For example, "x, y, and/or z" can refer to "x" alone, "y" alone, "z" alone, "x, y, and z," "(x and y) or z," "x or (y and z)," or "x or y or z." It is specifically contemplated that x, y, or z may be specifically excluded from an embodiment.

Throughout this application, the term "about" is used according to its plain and ordinary meaning in the area of cell and molecular biology to indicate that a value includes the standard deviation of error for the device or method being employed to determine the value.

As used herein, the term "autologous" refers to tissues or cells or other material that are obtained from the same individual.

As used herein, "allogeneic" refers to tissues or cells or other material from another body that in a natural setting are immunologically incompatible or capable of being immunologically incompatible, although from one or more individuals of the same species.

As used herein, the term "therapeutically effective amount" is synonymous with "effective amount", "therapeutically effective dose", and/or "effective dose" and refers to the amount of compound that will elicit the biological, cosmetic or clinical response being sought by the practitioner in an individual in need thereof. As one example, an effective amount is the amount sufficient to reduce immunogenicity of a group of cells. The appropriate effective amount to be administered for a particular application of the disclosed methods can be determined by those skilled in the art, using the guidance provided herein. For example, an effective amount can be extrapolated from in vitro and in vivo assays as described in the present specification. One skilled in the art will recognize that the condition of the individual can be monitored throughout the course of therapy and that the effective amount of a compound or composition disclosed herein that is administered can be adjusted accordingly.

"Muscle cell" as used herein refers to any cell which contributes to muscle tissue. Myoblasts, satellite cells, myotubes, and myofibril tissues are all included in the term "muscle cells" and may all be treated using the methods of the disclosure. Muscle cell effects may be induced within skeletal, cardiac and smooth muscles. Mitogenesis may be induced in muscle cells, including myoblasts or satellite cells, of skeletal muscle, smooth muscle or cardiac muscle. Mitogenesis as used herein refers to any cell division which results in the production of new muscle cells in the patient. More specifically, mitogenesis in vitro is defined as an increase in mitotic index relative to untreated cells of 50%, more preferably 100%, and most preferably 300%, when the cells are exposed to labelling agent for a time equivalent to two doubling times. The mitotic index is the fraction of cells in the culture which have labelled nuclei when grown in the presence of a tracer which only incorporates during S phase (i.e., BrdU) and the doubling time is defined as the average time required for the number of cells in the culture to increase by a factor of two).

The term "fibroblast" defines, intra alia, cells that are fibroblasts from various tissues, selected for specific properties associated with regenerative activity. "Fibroblasts", in some embodiments refers to a cell population comprising, consisting essentially of, or consisting of fibroblasts, including any modified or unmodified fibroblast described herein. As used herein, a "population of fibroblasts" may consist of only fibroblasts, including any fibroblasts described herein. Alternatively, as used herein, a "population of fibroblasts" may comprise fibroblasts along with other cell types and/or other compositions described herein. Tissues useful for the practice of the disclosure are generally tissues associated with regenerative activity. Said tissues include, as non-limiting examples, placenta, endometrial cells, Wharton's jelly, bone marrow, and adipose tissue. In certain embodiments, fibroblasts, are selected for expression of the markers CD117, CD105, and/or expression of the rhodamine 123 efflux activity. In some embodiments of the disclosure, fibroblasts are selected for expression of markers selected from the group consisting of Oct-4, CD-34, KLF-4, Nanog, Sox-2, Rex-1, GDF-3, Stella, possesses enhanced expression of GDF-11, and a combination thereof. Selection of fibroblasts for expression of said markers may be performed by initial expression of proteins found on the membrane of the cells, which result in possessing other markers mentioned. The fibroblasts of the disclosure may be cultured in media supplemented with platelet lysate (PL) and/or fetal calf serum (FCS). In particular embodiments of the disclosure, methods of producing fibroblasts that are muscle reparative are described.

The term "passaging" refers to the process of transferring a portion of cells from one culture vessel into a new culture vessel.

The term "cryopreserve" refers to preserving cells for long term storage in a cryoprotectant at low temperature.

The term "muscle regeneration" as used herein refers to the process by which new muscle fibers form from muscle progenitor cells. The useful therapeutic for regeneration confers an increase in the number of new fibers by at least 1%, more preferably by at least 20%, and most preferably by at least 50%, as defined above.

"Differentiation of muscle cells" as used herein refers to the induction of a muscle developmental program which specifies the components of the muscle fiber such as the contractile apparatus (the myofibril). The therapeutic useful for differentiation increases the quantity of any component of the muscle fiber in the diseased tissue by at least 10% or more, more preferably by 50% or more, and most preferably by more than 100% relative to the equivalent tissue in a similarly treated control animal.

"Atrophy of muscle" as used herein refers to a significant loss in muscle fiber girth. By significant atrophy is meant a reduction of muscle fiber diameter in diseased, injured or unused muscle tissue of at least 10% relative to undiseased, uninjured, or normally utilized tissue.

The terms "decrease," "reduce," "reduced," "reduction," "decrease," and "inhibit" are all used herein generally to mean a decrease by a statistically significant amount relative to a reference. However, for avoidance of doubt, "reduce," "reduction" or "decrease" or "inhibit" typically means a decrease by at least 10% as compared to a reference level and can include, for example, a decrease by at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95%, at least about 98%, at least about 99%, up to and including, for example, the complete absence of the given entity or parameter as compared to the reference level, or any decrease between 10-99% as compared to the absence of a given treatment.

The terms "increased," "increase" or "enhance" or "activate" are all used herein to generally mean an increase by a statically significant amount; for the avoidance of any doubt, the terms "increased", "increase" or "enhance" or "activate" means an increase of at least 10% as compared to a reference level, for example an increase of at least about 20%, or at least about 30%, or at least about 40%, or at least about 50%, or at least about 60%, or at least about 70%, or at least about 80%, or at least about 90%, or up to and including a 100% increase or any increase between 10-100% as compared to a reference level, or at least about a 2-fold, or at least about a 3-fold, or at least about a 4-fold, or at least about a 5-fold or at least about a 10-fold increase, or any increase between 2-fold and 10-fold or more as compared to a reference level.

II. Cell Population Characterization and Preparation

The starting material for the fibroblasts may be various tissues, and in certain embodiments, starting tissue is or comprises skin cells obtained from cosmetic surgery. In other embodiments, bone marrow, placenta, umbilical cord, mobilized peripheral blood, and/or omentum is isolated from healthy donors. In particular embodiments, these donors are mammals, such as humans. In one embodiment of the method of producing fibroblasts of the disclosure, fibroblasts (including dermal derived fibroblasts) are cultured in tissue culture flasks between 2 and 10 days prior to washing non-adherent cells from the flask. Optionally, the number of days of culture of dermal fibroblast cells prior to washing non-adherent cells is 2 to 3 days. Preferably the fibroblasts are cultured in platelet lysate (PL) containing media. For example, 300 µl of fibroblasts is cultured in 15 ml of PL supplemented medium in T75 or other adequate tissue culture vessels. After washing away the non-adherent cells, the adherent cells are also cultured in media that has been supplemented with platelet lysate (PL). Thrombocytes are a well characterized human product which a is widely used in clinics for patients in need of blood supplement. Thrombocytes are known to produce a wide variety of factors, e.g. PDGF-BB, TGF-beta, IGF-1, and VEGF. In one embodiment of the method of producing fibroblasts of the disclosure, an optimized preparation of PL is used. This optimized preparation of PL is made up of pooled platelet rich plasmas (PRPs) from at least 10 donors (to equalize for differences in cytokine concentrations) with a minimal concentration of $3 \times 10^9$ thrombocytes/ml.

In certain embodiments, fibroblasts and/or endothelial cells may be derived from tissues comprising skin, heart, blood vessels, bone marrow, skeletal muscle, liver, pancreas, brain, adipose tissue, foreskin, placental, and/or umbilical cord. In specific embodiments, the fibroblasts are placental, fetal, neonatal or adult or mixtures thereof.

In certain embodiments, fibroblasts are gene edited, and/or gene silenced in order to suppress expression of insulin growth factor binding protein (IGFBP-5). IGFBP-5 may be silenced in order to reduce satellite cell inhibiting activity of fibroblasts derived from DMD patients and/or healthy donors [79-81]. In certain embodiments, fibroblasts are genetically modified to express dystrophin, uterin, regenerative genes (such as PAX7), anti-apoptotic genes (such as survivin, bc1-2, and bc1-2xL), as well as anti-inflammatory genes (such as IL-4, IL-10, IL-13, IL-20, IL-35, and IL-37), or a combination thereof.

III. Cell Population Administration

Certain embodiments of the disclosure concern the administration of fibroblasts, either unmanipulated or manipulated, as a cellular therapeutic for treatment of a muscular dystrophy. In one embodiment, the muscular dystrophy is Duchenne Muscular Dystrophy. In some embodiments of the disclosure, fibroblasts are administered systemically in a manner to increase expression of functional dystrophin protein into cells of the body, although in other cases the administration is local. In certain embodiments, fibroblasts are administered intramuscularly and systemically. The fibroblasts may be concurrently administered intramuscularly and systemtically. The fibroblasts may be administered intramuscularly then systemically, or administered systemically then intramuscularly. In particular embodiments of the disclosure, fibroblasts are administered to an individual by any suitable route, including by injection (such as intramuscular injection), including in hypoxic areas. Suitable routes include intravenous, subcutaneous, intrathecal, oral, intrarectal, intrathecal, intra-omental, intraventricular, intrahepatic, and intrarenal, as examples.

The number of administrations of cells to an individual will depend upon the factors described herein at least in part and may be optimized using routine methods in the art. In specific embodiments, a single administration is required. In other embodiments, a plurality of administration of cells is required. It should be appreciated that the system is subject to variables, such as the particular need of the individual, which may vary with time and circumstances, the rate of loss of the cellular activity as a result of loss of cells or activity of individual cells, and the like. Therefore, it is expected that each individual could be monitored for the proper dosage, and such practices of monitoring an individual are routine in the art.

For treatment of muscular dystrophies one may address the muscular degeneration that appears to be a multifactorial process in which numerous types of intervention may be envisioned. In some embodiments, fibroblasts are used for administration of one or more corrective genes, either through wild type expression or induced overexpression, and/or for anti-inflammatory effects. Although induction of dystrophin expression is paramount to cure and/or treat muscular dystrophies, it appears that inflammatory events secondary to myocyte dystrophin mutation also play a major role in disease progression. Intense exercise in wild-type muscles is associated with transient inflammation [37], which is part of a homeostatic process. In contrast, DMD patients are believed to have a prolonged inflammatory milieu subsequent to muscular strain, which appears to contribute to muscle deterioration [38]. The administration of fibroblasts may enhance regeneration and reduce inflammation. Specifically suppressing inflammation using fibroblasts may be performed using fibroblasts cultured in media that endows anti-inflammatory activities, or can be induced by using fibroblasts that are transfected with anti-inflammatory genes such as IL-4, IL-10, IL-20, IL-35, and/or IL-37. Clinically, DMD onset and progression are known to be associated with upregulation of inflammatory genes [39, 40], which has been confirmed by microarray studies in the MDX mouse model of DMD [41]. It is known that the inflammatory-associated transcription factor NF-kB is upregulated in muscles of both animal models and patients with DMD and that its inhibition in the MDX model results in therapeutic benefit by decreasing macrophage infiltration and permitting a higher level of myogenesis [42]. At the protein level, inflammatory mediators such as TNF-alpha have been detected at elevated systemic levels as compared to healthy controls [43]. In fact, inhibition of TNF-alpha with clinically-used agents such as Etanercept or Remicade has been demonstrated to diminish muscle deterioration in the MDX mouse [44, 45]. It is therefore conceivable that soluble inflammatory factors contribute to progression of degeneration by direct inhibition of muscle function [46], as well as elicitation of immunological cells to area of muscle damage [47]. Accordingly, in some embodiments, fibroblasts are used together with antibodies to inflammatory agents such as TNF-alpha. Additionally, in some embodiments, fibroblasts are used as an adjuvant or stimulator of anti-inflammatory cells including T regulatory cells, myeloid derived suppressor cells, M2 macrophages, N2 neutrophils, mesenchymal stem cells, and Th2 cells.

In particular embodiments, fibroblasts are administered to an individual to reduce local inflammation. The possibility that local inflammation is occurring as muscle damage progresses may be confirmed at a cellular level by observations of immune cell infiltration, such as in biopsies from the muscle of the individual. For example, monocytic infiltration occurs with such selectivity to degenerating muscles that these cells have been proposed as vectors for delivery of gene therapy [48]. In particular embodiments, fibroblasts are used to deliver one or more genes to the area of damaged muscle. Genes to be delivered include dystrophin, uterin, regenerative genes (such as PAX7), anti-apoptotic genes (such as survivin, bc1-2, and/or bc1-2xL), as well as anti-inflammatory genes (such as IL-4, IL-10, IL-13, IL-20, IL-35, and/or IL-37). In certain embodiments, fibroblasts are genetically modified to express dystrophin, uterin, regenerative genes (such as PAX7), anti-apoptotic genes (such as survivin, bc1-2, and/or bc1-2xL), as well as anti-inflammatory genes (such as IL-4, IL-10, IL-13, IL-20, IL-35, and/or IL-37).

In particular embodiments, fibroblasts are used as a therapeutic to prevent inflammatory cells from entering muscle. Fibroblasts may be administered in a manner to decrease cytokines and other chemokines associated with immunocyte infiltration into muscle. The cytokines IL-6, MCP-1, and IP-10 have been previously discussed as mediators [20]. The disclosure teaches decreasing of these cytokines by fibroblast administration. It has been reported that in the diaphragm of the MDX mouse, which is one of the muscles most injured due to repeated physical activity, MIP-1 alpha and RANTES are expressed by the muscle itself [49]. Accordingly, in one aspect of the disclosure suppression of these chemokines is described by administration of fibroblasts. Furthermore, other studies have confirmed expression of these, and also the monocyte-chemoattractant CCL6 in dystrophic limb muscle, thus suggesting upregulation of chemokine synthesis may be a systemic occurrence in DMD [47]. Actual transmigration of monocytes may be mediated by VCAM-1 expression on the endothelium, which has previously been shown to attract CD133 positive stem cells into exercised dystrophic muscle [50], but is also a known ligand for leukocyte expressed VLA-4.

Further involved in the self-perpetuating inflammatory cascade is the renin-angiotensin system that increases the fibrotic cytokine TGF-beta [51], and upregulation of TNF-alpha that is directly toxic to myocytes [52, 53]. In certain embodiments, fibroblasts are administered to decrease TGF-beta, and/or TNF-alpha production from muscle and/or adjacent cells. The disclosure encompasses the paradoxical effect of fibroblast administration providing an antifibrotic effect. The increased fibrotic state of muscles in DMD is associated with upregulated expression of MMP inhibitors such as TIMP1 and TIMP2 in patients [54]. Modification of the MMP/TIMP ratio by administration of MMP overexpressing cells has yielded therapeutic benefit in the mdx model, which were associated with increased neovascularization [55]. In fact, altered blood vessels were cited as a possible cause of DMD in historical literature [56]. In some embodiments, fibroblasts, including unmodified and/or modified fibroblasts, are used to alter MMP/TIMP ratio.

In some embodiments, the administration of fibroblasts induces a manipulation of macrophages. Specifically, fibroblasts, treated or untreated, may be administered to alter macrophage phenotype from M1 to M2. It is known that macrophages are critical for angiogenesis, tissue regeneration, and reduction of fibrosis [57]. In the context of DMD macrophages play both a reparative and destructive role depending on context. Broadly speaking there are two types of macrophages distinguished based on cytokine production and arginine metabolism. M1 macrophages are primarily antiangiogenic, characterized by high levels of nitric oxide production, and possess cytotoxic activity, whereas M2 macrophages generally are anti-inflammatory, support angiogenesis, and associated with tissue repair [58]. This concept has been demonstrated in situations such as cancer, in which M2 tumor infiltrating macrophages play an important role in neovascularization and immune evasion [59]. In contrast, stimulation of M1 macrophages has been shown to inhibit tumor growth [60]. This dual ability of macrophages to promote either damage or healing has been observed in other biological systems, for example, administration of M1 macrophages accelerates adriamycin-induced kidney failure whereas M2 macrophages are protective [61]. In certain embodiments, the manipulation of macrophages polarization is used to treat muscular dystrophies. Specifically, polarization is desired to shift macrophages to an M2 phenotype in DMD in order to promote muscle healing. In contrast, M1 macrophages promote muscle death. In the context of DMD, M1-like macrophages are found infiltrating the dystrophic muscle, and inhibition of this phenotype through blockade of the NF-kB pathway results in amelioration of disease [42]. Another method of altering the M1 to M2 macrophage state is through exposure to the cytokine IL-10. Treatment of macrophages with this cytokine reduces ability to cause muscle damage and augments regenerative activity through alteration of arginine metabolism to reduce nitric oxide production and augment polyamine synthesis [20]. The dual role of macrophages is further supported by studies in which macrophage conditioned media, in absence of inflammatory stimuli, was capable of eliciting ex vivo myoblast expansion [62]. These examples are provided to teach one of skill in the art means of utilizing macrophage manipulation by fibroblasts as therapeutic intervention.

In some embodiments, fibroblasts are utilized to inhibit pathological T cell immunity. T cell immunity is also known to contribute to DMD progression. Suggesting this possibility at a clinical level, Kissel et al found that in a double-blind trial of prednisone significant decreases in lymphocytic infiltrates in muscle biopsies were observed in the treated but not control patients [63]. These clinical observations have also been described in animal studies where immune suppressants such as cyclosporine A, which targets T cells, have been demonstrated to reduce progression of pathology [64]. T cells are believed to be associated with stimulation of TGF-b and augmentation of fibrosis. For example, it was demonstrated that depletion of T and B cells results in reduction of myocytic damage in SCID mice that have been bred onto the MDX background [65]. Studies in which thymic tissue was transplanted into T cell deficient MDX mice confirmed the critical role of T cells in fibrosis [66]. Dystrophic muscles express upregulate expression of MHC I [67, 68], which may be the result of local inflammatory cell activation. There is some evidence of a direct autoimmune component in DMD in that IgG anti-muscle antibodies, indicating class-switching had occurred [69]. In fact, some studies suggest that muscular inflammation may be transferred into naïve recipients by administration of T cells from dystrophic mice together with muscle extracts [70]. These data would suggest the T cell compartment not only acts as a passive response to dystrophic injury but may play a more substantial role. Mechanistically, T cells appear to mediate muscle damage through secretion of osteopontin [71], which promotes fibrosis, as well as direct perforin-mediated cytotoxicity [72].

In particular embodiments, fibroblasts are administered to an individual in order to augment muscle regeneration in the individual with an absence of inflammation or with suppressed inflammation. It is known that muscle tissue in adult vertebrates regenerate from reserve myoblasts called satellite cells [15, 73]. Satellite cells are distributed throughout muscle tissue and are mitotically quiescent in the absence of injury or disease. Following muscle injury or during recovery from disease, satellite cells will reenter the cell cycle, proliferate and 1) enter existing muscle fibers or 2) undergo differentiation into multinucleate myotubes which form new muscle fiber. The myoblasts ultimately yield replacement muscle fibers or fuse into existing muscle fibers, thereby increasing fiber girth by the synthesis of contractile apparatus components [74]. This process is illustrated, for example, by the nearly complete regeneration which occurs in mammals following induced muscle fiber degeneration; the muscle progenitor cells proliferate and fuse together regenerating muscle fibers. In some embodiments, administration of fibroblasts augments muscle regeneration, stimulates satellite cell anti-apoptotic activity, and/or allows for enhanced muscle formation/preservation.

In some embodiments, the administration of the population of cells causes an increase in satellite cell activation as measured by the appearance of labelled satellite cells in the muscle tissue of an individual exposed to a tracer which only incorporates during S phase (i.e., BrdU). In some embodiments, a population of cells, administered to an individual, increases satellite cell activation relative to a control individual by at least 10%, at least 50%, or by more than 200% when the individual is exposed to labelling agent for a period of greater than 15 minutes and tissues are assayed between 10 hours and 24 hours after administration of the population at a therapeutic dose. Alternatively, satellite cell activation in vivo by administration of fibroblasts may be detected by monitoring the appearance of the intermediate filament vimentin by immunological or RNA analysis methods. When vimentin is assayed, a therapeutically effective dose of the population of cells may be defined as one which causes expression of detectable levels of vimentin in the muscle tissue when the therapeutically useful dosage is provided. Myogenesis as used herein refers to any fusion of myoblasts to yield myotubes. Most preferably, an effect on myogenesis is defined as an increase in the fusion of myoblasts and the enablement of the muscle differentiation program. The useful myogenic therapeutic is defined as a compound which confers any increase in the fusion index in vitro. the compound may confer at least a 2.0-fold increase. The compound may confer a 3.0-fold or greater increase in the fusion index relative to the control. The fusion index is defined as the fraction of nuclei present in multinucleated cells in the culture relative to the total number of nuclei present in the culture. The percentages provided above are for cells assayed after 6 days of exposure to the myogenic compound and are relative to an untreated control. Myogenesis may also be determined by assaying the number of nuclei per area in myotubes or by measurement of the levels of muscle specific protein by Western analysis. The compound may confer at least a 2.0-fold increase in the density of myotubes using the assay provided, for example, herein. The compound may confer a 3.0-fold or greater increase.

In certain embodiments, fibroblasts, either unmodified or modified, induce both the proliferation of muscle cells and the differentiation and survival of myotubes. In particular embodiments, fibroblasts derived proteins are used as growth factors to induce the mitogenesis, survival, growth and differentiation of muscle cells. Treating of the muscle cells to achieve these effects may be achieved by contacting muscle cells with a polypeptide described herein, such as FGF1 or FGF2. These factors may be used to produce muscle cell mitogenesis, differentiation, and survival in an individual by administering to the individual an effective amount of a polypeptide or a related compound. IL-10 has been shown to possess antifibrotic activity and its addition to the current fibroblast treatment protocol is envisioned [99]. In some embodiments, IL-10 is transferred into fibroblasts using similar techniques for transfection of mesenchymal stem cells, which are known in the literature and incorporated by reference [100]. The IL-10 transfected fibroblasts may be utilized for localized and/or administration into individuals suffering from muscular dystrophy. In some embodiments, an antioxidant is added to the fibroblast administration regimen. The antioxidant may be a composition selected from the group consisting of a) n-acetylcysteine; b) intravenous ascorbic acid; c) pterostilbene; d) vitamin k3; e) resveratrol; f) alpha lipoic acid; g) quercetin; h) kaempferol; i) myricetin; j) apigenin; k) luteolin; l) curcumin; m) caffeic acid; and n) a combination thereof.

In some embodiments, administration of fibroblasts induces an increase in the fiber size and/or by increases the number of fibers. The growth of muscle as used herein may be measured by a) an increase in wet weight, b) an increase in protein content, c) an increase in the number of muscle fibers, or d) an increase in muscle fiber diameter. An increase in growth of a muscle fiber can be defined as an increase in the diameter where the diameter is defined as the minor axis of ellipsis of the cross section. The fibroblasts may increase the wet weight, protein content and/or diameter by 10% or more, by more than 50%, or by more than 100% in an individual whose muscles have been previously degenerated by at least 10% and relative to a similarly treated control individual (for example, an individual with degenerated muscle tissue which is not treated with the muscle growth compound). A dose of fibroblasts which increases growth by increasing the number of muscle fibers may be a therapeutically effective amount of fibroblasts when it increases the number of fibers in the diseased tissue by at least 1%, at least 20%, or by at least 50%. These percentages are determined relative to the basal level in a comparable untreated undiseased individual or in the contralateral undiseased muscle when the compound is administered and acts locally.

In some embodiments, the administration of fibroblasts prevents a loss of muscle fibers as evidenced by a lack of necrosis and/or apoptosis, and/or the prevention of other mechanisms of muscle fiber loss. The decrease in the rate of cell death may be a decrease of at least 10%, at least 50%, or at least 300% relative to an untreated control. The rate of survival may be measured by counting cells stainable with a dye specific for dead cells (such as propidium iodide) in culture when the cells are 8 days post-differentiation (i.e., 8 days after the media is changed from 20% to 0.5% serum).

The fibroblasts may be administered together with one or more various growth factors. For example, several growth factors which regulate the proliferation and differentiation of adult (and embryonic) myoblast. These include fibroblast growth factor (FGF) which is mitogenic for muscle cells and is an inhibitor of muscle differentiation. Transforming growth factor beta (TGF-beta) has no effect on myoblast proliferation, but is an inhibitor of muscle differentiation. Insulin-like growth factors (IGFs) have been shown to stimulate both myoblast proliferation and differentiation in rodents. Platelet derived growth factor (PDGF) is also mitogenic for myoblasts and is a potent inhibitor of muscle cell differentiation. These growth factors may be administered together with fibroblasts, or may be administered in the form of gene transfected fibroblasts.

In particular embodiments, fibroblasts which naturally, or after manipulation, express IGF, are administered in order to stimulate satellite cell proliferation and protection from apoptosis. The positive impact of IGF on muscle satellite cells has previously been described [75-78].

In some embodiments, fibroblasts are administered together with one or more inhibitors of NF-kappaB kinase 2 (IKK2) [82]. Such inhibition may be performed by chemical, antisense, RNA interference inducing means, and/or gene editing means.

In some embodiments, fibroblasts are administered with endothelial and/or endothelial progenitor cells in order to enhance engraftment and function of said fibroblasts and fibroblast associated muscle tissue [83]. In certain embodiments, administration of hyperbaric oxygen is utilized together with administration of fibroblasts in order to augment regenerative effect of administered fibroblasts. In some embodiments, hyperbaric oxygen is used to augment levels of cytokines such as IGF-1 [84]. Protocols for the use of hyperbaric oxygen in muscle regeneration are published and incorporated by reference [85-92]. In some embodiments, hyperbaric oxygen is used together with or substituted with ozone therapy, protocols for which are known and incorporated by reference [93-98].

The disclosure encompasses administration of fibroblasts, and/or modified fibroblasts that increases mitogenesis, differentiation and survival of muscle cells, which induces expression of proteins such as glial growth factors, acetyl- choline receptor inducing activity (ARIA), heregulins, neu differentiation factor, and, more generally, neuregulins.

IV. Kits of the Disclosure

Any of the cellular and/or non-cellular compositions described herein or similar thereto may be comprised in a kit. In a non-limiting example, one or more reagents for use in methods for preparing cellular therapy may be comprised in a kit. The kit may comprise any protein listed in the disclosure. The kit components are provided in suitable container means.

Some components of the kits may be packaged either in aqueous media or in lyophilized form. The container means of the kits will generally include at least one vial, test tube, flask, bottle, syringe or other container means, into which a component may be placed, and preferably, suitably aliquoted. Where there are more than one component in the kit, the kit also will generally contain a second, third or other additional container into which the additional components may be separately placed. However, various combinations of components may be comprised in a vial. The kits of the present disclosure also will typically include a means for containing the components in close confinement for commercial sale. Such containers may include injection or blow molded plastic containers into which the desired vials are retained.

When the components of the kit are provided in one and/or more liquid solutions, the liquid solution is an aqueous solution, with a sterile aqueous solution being particularly useful. In some cases, the container means may itself be a syringe, pipette, and/or other such like apparatus, or may be a substrate with multiple compartments for a desired reaction.

Some components of the kit may be provided as dried powder(s). When reagents and/or components are provided as a dry powder, the powder can be reconstituted by the addition of a suitable solvent. It is envisioned that the solvent may also be provided in another container means. The kits may also comprise a second container means for containing a sterile acceptable buffer and/or other diluent.

In specific embodiments, reagents and materials include primers for amplifying desired sequences, nucleotides, suitable buffers or buffer reagents, salt, and so forth, and in some cases the reagents include apparatus or reagents for isolation of a particular desired cell(s).

In particular embodiments, there are one or more apparatuses in the kit suitable for extracting one or more samples from an individual. The apparatus may be a syringe, fine needles, scalpel, and so forth.

REFERENCES

The following references, to the extent that they provide exemplary procedural or other details supplementary to those set forth herein, are specifically incorporated herein by reference.

1. Barlow, Y. and J. Willoughby, *Pathophysiology of soft tissue repair.* Br Med Bull, 1992. 48(3): p. 698-711.

2. Lehto, M. U. and M. J. Jarvinen, *Muscle injuries, their healing process and treatment.* Ann Chir Gynaecol, 1991. 80(2): p. 102-8.

3. Brioche, T., et al., *Muscle wasting and aging: Experimental models, fatty infiltrations, and prevention.* Mol Aspects Med, 2016. 50: p. 56-87.

4. Riddle, E. S., M. H. Stipanuk, and A. E. Thalacker-Mercer, *Amino acids in healthy aging skeletal muscle.* Front Biosci (Elite Ed), 2016. 8: p. 326-50.

5. Tagliaferri, C., et al., *Muscle and bone, two interconnected tissues.* Ageing Res Rev, 2015. 21: p. 55-70.

6. Migliaccio, S., et al., *Age-associated (cardio)metabolic diseases and cross-talk between adipose tissue and skeleton: endocrine aspects.* Horm Mol Biol Clin Investig, 2014. 20(1): p. 25-38.

7. Kostek, M. C. and M. J. Delmonico, *Age-related changes in adult muscle morphology.* Curr Aging Sci, 2011. 4(3): p. 221-33.

8. Nakamura, A., *Mutation-Based Therapeutic Strategies for Duchenne Muscular Dystrophy: From Genetic Diagnosis to Therapy.* J Pers Med, 2019. 9(1).

9. Morales, J. A. and K. Mahajan, *Dystrophinopathies*, in *StatPearls*. 2018: Treasure Island (Fla.).

10. Matsumura, K. and K. P. Campbell, *Dystrophin-glycoprotein complex: its role in the molecular pathogenesis of muscular dystrophies.* Muscle Nerve, 1994. 17(1): p. 2-15.

11. Ohlendieck, K., et al., *Dystrophin-glycoprotein complex is highly enriched in isolated skeletal muscle sarcolemma.* J Cell Biol, 1991. 112(1): p. 135-48.

12. Ohlendieck, K., et al., *Duchenne muscular dystrophy: deficiency of dystrophin-associated proteins in the sarcolemma.* Neurology, 1993. 43(4): p. 795-800.

13. Reggiani, C., *Between channels and tears: aim at ROS to save the membrane of dystrophic fibres.* J Physiol, 2008. 586(7): p. 1779.

14. Ervasti, J. M., et al., *Deficiency of a glycoprotein component of the dystrophin complex in dystrophic muscle.* Nature, 1990. 345(6273): p. 315-9.

15. Campion, D. R., *The muscle satellite cell: a review.* Int Rev Cytol, 1984. 87: p. 225-51.

16. Stuelsatz, P., P. Keire, and Z. Yablonka-Reuveni, *Isolation, Culture, and Immunostaining of Skeletal Muscle Myofibers from Wildtype and Nestin-GFP Mice as a Means to Analyze Satellite Cell.* Methods Mol Biol, 2017. 1556: p. 51-102.

17. Motohashi, N. and A. Asakura, *Muscle satellite cell heterogeneity and self-renewal.* Front Cell Dev Biol, 2014. 2: p. 1.

18. Jensen, L., et al., *Muscular response to the first three months of deflazacort treatment in boys with Duchenne muscular dystrophy.* J Musculoskelet Neuronal Interact, 2017. 17(2): p. 8-18.

19. Chadwick, J. A., et al., *Myeloid cells are capable of synthesizing aldosterone to exacerbate damage in muscular dystrophy.* Hum Mol Genet, 2016. 25(23): p. 5167-5177.

20. Villalta, S. A., et al., *Shifts in macrophage phenotypes and macrophage competition for arginine metabolism affect the severity of muscle pathology in muscular dystrophy.* Hum Mol Genet, 2009. 18(3): p. 482-96.

21. Villalta, S. A., et al., *Interleukin-10 reduces the pathology of mdx muscular dystrophy by deactivating M1 macrophages and modulating macrophage phenotype.* Hum Mol Genet, 2011. 20(4): p. 790-805.

22. Miller, J. B., L. Schaefer, and J. A. Dominov, *Seeking muscle stem cells.* Curr Top Dev Biol, 1999. 43: p. 191-219.

23. Lund, T. C., R. W. Grange, and D. A. Lowe, *Telomere shortening in diaphragm and tibialis anterior muscles of aged mdx mice.* Muscle Nerve, 2007. 36(3): p. 387-90.

24. Merrick, D., et al., *Muscular dystrophy begins early in embryonic development deriving from stem cell loss and disrupted skeletal muscle formation.* Dis Model Mech, 2009.

25. Cossu, G. and F. Mavilio, *Myogenic stem cells for the therapy of primary myopathies: wishful thinking or therapeutic perspective?* J Clin Invest, 2000. 105(12): p. 1669-74.

26. Spuler, S. and A. G. Engel, *Unexpected sarcolemmal complement membrane attack complex deposits on nonnecrotic muscle fibers in muscular dystrophies.* Neurology, 1998. 50(1): p. 41-6.

27. Eagle, M., et al., *Survival in Duchenne muscular dystrophy: improvements in life expectancy since 1967 and the impact of home nocturnal ventilation.* Neuromuscul Disord, 2002. 12(10): p. 926-9.

28. Fenichel, G. M., et al., *Long-term benefit from prednisone therapy in Duchenne muscular dystrophy.* Neurology, 1991. 41(12): p. 1874-7.

29. Romero, N. B., et al., *Phase I study of dystrophin plasmid-based gene therapy in Duchenne/Becker muscular dystrophy.* Hum Gene Ther, 2004. 15(11): p. 1065-76.

30. van Deutekom, J. C., et al., *Local dystrophin restoration with antisense oligonucleotide PRO051.* N Engl J Med, 2007. 357(26): p. 2677-86.

31. Torrente, Y., et al., *Autologous transplantation of muscle-derived CD133+ stem cells in Duchenne muscle patients.* Cell Transplant, 2007. 16(6): p. 563-77.

32. Law, P. K., et al., *Feasibility, safety, and efficacy of myoblast transfer therapy on Duchenne muscular dystrophy boys.* Cell Transplant, 1992. 1(2-3): p. 235-44.

33. Mendell, J. R., et al., *Myoblast transfer in the treatment of Duchenne's muscular dystrophy.* N Engl J Med, 1995. 333(13): p. 832-8.

34. Skuk, D., et al., *First test of a "high-density injection" protocol for myogenic cell transplantation throughout large volumes of muscles in a Duchenne muscular dystrophy patient: eighteen months follow-up.* Neuromuscul Disord, 2007. 17(1): p. 38-46.

35. Skuk, D., et al., *Dystrophin expression in muscles of duchenne muscular dystrophy patients after high-density injections of normal myogenic cells.* J Neuropathol Exp Neurol, 2006. 65(4): p. 371-86.

36. Skuk, D., et al., *Dystrophin expression in myofibers of Duchenne muscular dystrophy patients following intramuscular injections of normal myogenic cells.* Mol Ther, 2004. 9(3): p. 475-82.

37. Ispirlidis, I., et al., *Time-course of changes in inflammatory and performance responses following a soccer game.* Clin J Sport Med, 2008. 18(5): p. 423-31.

38. Gosselin, L. E. and K. M. McCormick, *Targeting the immune system to improve ventilatory function in muscular dystrophy.* Med Sci Sports Exerc, 2004. 36(1): p. 44-51.

39. Chen, Y. W., et al., *Expression profiling in the muscular dystrophies: identification of novel aspects of molecular pathophysiology.* J Cell Biol, 2000. 151(6): p. 1321-36.

40. Evans, N. P., et al., *Dysregulated intracellular signaling and inflammatory gene expression during initial disease onset in Duchenne muscular dystrophy.* Am J Phys Med Rehabil, 2009. 88(6): p. 502-22.

41. Marotta, M., et al., *Muscle genome-wide expression profiling during disease evolution in mdx mice.* Physiol Genomics, 2009. 37(2): p. 119-32.

42. Acharyya, S., et al., *Interplay of IKK/NF-kappaB signaling in macrophages and myofibers promotes muscle degeneration in Duchenne muscular dystrophy.* J Clin Invest, 2007. 117(4): p. 889-901.

43. Porreca, E., et al., *Haemostatic abnormalities, cardiac involvement and serum tumor necrosis factor levels in X-linked dystrophic patients.* Thromb Haemost, 1999. 81(4): p. 543-6.

44. Pierno, S., et al., *Role of tumour necrosis factor alpha, but not of cyclo-oxygenase-2-derived eicosanoids, on functional and morphological indices of dystrophic progression*

45. Grounds, M. D. and J. Torrisi, *Anti-TNFalpha (Remicade) therapy protects dystrophic skeletal muscle from necrosis.* FASEB J, 2004. 18(6): p. 676-82.

46. Grounds, M. D., et al., *Implications of cross-talk between tumour necrosis factor and insulin-like growth factor-1 signalling in skeletal muscle.* Clin Exp Pharmacol Physiol, 2008. 35(7): p. 846-51.

47. Porter, J. D., et al., *Persistent over-expression of specific CC class chemokines correlates with macrophage and T-cell recruitment in mdx skeletal muscle.* Neuromuscul Disord, 2003. 13(3): p. 223-35.

48. Parrish, E. P., et al., *Targeting widespread sites of damage in dystrophic muscle: engrafted macrophages as potential shuttles.* Gene Ther, 1996. 3(1): p. 13-20.

49. Demoule, A., et al., *Expression and regulation of CC class chemokines in the dystrophic (mdx) diaphragm.* Am J Respir Cell Mol Biol, 2005. 33(2): p. 178-85.

50. Gavina, M., et al., *VCAM-1 expression on dystrophic muscle vessels has a critical role in the recruitment of human blood-derived CD133+ stem cells after intra-arterial transplantation.* Blood, 2006. 108(8): p. 2857-66.

51. Sun, G., et al., *Intramuscular renin-angiotensin system is activated in human muscular dystrophy.* J Neurol Sci, 2009.

52. Radley, H. G., M. J. Davies, and M. D. Grounds, *Reduced muscle necrosis and long-term benefits in dystrophic mdx mice after cV1q (blockade of TNF) treatment.* Neuromuscul Disord, 2008. 18(3): p. 227-38.

53. Hodgetts, S., et al., *Reduced necrosis of dystrophic muscle by depletion of host neutrophils, or blocking TNFalpha function with Etanercept in mdx mice.* Neuromuscul Disord, 2006. 16(9-10): p. 591-602.

54. von Moers, A., et al., *Increased mRNA expression of tissue inhibitors of metalloproteinase-1 and -2 in Duchenne muscular dystrophy.* Acta Neuropathol, 2005. 109(3): p. 285-93.

55. Gargioli, C., et al., *PlGF-MMP-9-expressing cells restore microcirculation and efficacy of cell therapy in aged dystrophic muscle.* Nat Med, 2008. 14(9): p. 973-8.

56. Musch, B. C., et al., *A comparison of the structure of small blood vessels in normal, denervated and dystrophic human muscle.* J Neurol Sci, 1975. 26(2): p. 221-34.

57. Pollard, J. W., *Trophic macrophages in development and disease.* Nat Rev Immunol, 2009. 9(4): p. 259-70.

58. Martinez, F. O., et al., *Macrophage activation and polarization.* Front Biosci, 2008. 13: p. 453-61.

59. Sica, A., et al., *Macrophage polarization in tumour progression.* Semin Cancer Biol, 2008. 18(5): p. 349-55.

60. Eriksson, F., et al., *Tumor-specific bacteriophages induce tumor destruction through activation of tumor-associated macrophages.* J Immunol, 2009. 182(5): p. 3105-11.

61. Wang, Y., et al., *Ex vivo programmed macrophages ameliorate experimental chronic inflammatory renal disease.* Kidney Int, 2007. 72(3): p. 290-9.

62. Malerba, A., et al., *Macrophage-secreted factors enhance the in vitro expansion of DMD muscle precursor cells while preserving their myogenic potential.* Neurol Res, 2008.

63. Kissel, J. T., et al., *Mononuclear cell analysis of muscle biopsies in prednisone-treated and untreated Duchenne muscular dystrophy.* CIDD Study Group. Neurology, 1991. 41(5): p. 667-72.

64. De Luca, A., et al., *A multidisciplinary evaluation of the effectiveness of cyclosporine a in dystrophic mdx mice.* Am J Pathol, 2005. 166(2): p. 477-89.

65. Farini, A., et al., *T and B lymphocyte depletion has a marked effect on the fibrosis of dystrophic skeletal muscles in the scid/mdx mouse.* J Pathol, 2007. 213(2): p. 229-38.

66. Morrison, J., et al., *T-cell-dependent fibrosis in the mdx dystrophic mouse.* Lab Invest, 2000. 80(6): p. 881-91.

67. Confalonieri, P., et al., *Muscle inflammation and MHC class I up-regulation in muscular dystrophy with lack of dysferlin: an immunopathological study.* J Neuroimmunol, 2003. 142(1-2): p. 130-6.

68. McDouall, R. M., M. J. Dunn, and V. Dubowitz, *Expression of class I and class II MHC antigens in neuromuscular diseases.* J Neurol Sci, 1989. 89(2-3): p. 213-26.

69. Laszlo, A., et al., *Antinuclear factor, smooth and striated muscle antibodies in Duchenne-type muscular dystrophy.* Acta Paediatr Hung, 1983. 24(4): p. 331-6.

70. Spencer, M. J., et al., *Helper (CD4(+)) and cytotoxic (CD8(+)) T cells promote the pathology of dystrophin-deficient muscle.* Clin Immunol, 2001. 98(2): p. 235-43.

71. Vetrone, S. A., et al., *Osteopontin promotes fibrosis in dystrophic mouse muscle by modulating immune cell subsets and intramuscular TGF-beta.* J Clin Invest, 2009. 119(6): p. 1583-94.

72. Spencer, M. J., et al., *Myonuclear apoptosis in dystrophic mdx muscle occurs by perforin-mediated cytotoxicity.* J Clin Invest, 1997. 99(11): p. 2745-51.

73. Chou, S. M. and I. Nonaka, *Satellite cells and muscle regeneration in diseased human skeletal muscles.* J Neurol Sci, 1977. 34(1): p. 131-45.

74. Schultz, E., D. L. Jaryszak, and C. R. Valliere, *Response of satellite cells to focal skeletal muscle injury.* Muscle Nerve, 1985. 8(3): p. 217-22.

75. Jennische, E., A. Skottner, and H. A. Hansson, *Satellite cells express the trophic factor IGF-I in regenerating skeletal muscle.* Acta Physiol Scand, 1987. 129(1): p. 9-15.

76. Adams, G. R. and S. A. McCue, *Localized infusion of IGF-I results in skeletal muscle hypertrophy in rats.* J Appl Physiol (1985), 1998. 84(5): p. 1716-22.

77. Barton-Davis, E. R., D. I. Shoturma, and H. L. Sweeney, *Contribution of satellite cells to IGF-I induced hypertrophy of skeletal muscle.* Acta Physiol Scand, 1999. 167(4): p. 301-5.

78. Hill, M. and G. Goldspink, *Expression and splicing of the insulin-like growth factor gene in rodent muscle is associated with muscle satellite (stem) cell activation following local tissue damage.* J Physiol, 2003. 549(Pt 2): p. 409-18.

79. Melone, M. A., et al., *Increased expression of IGF-binding protein-5 in Duchenne muscular dystrophy (DMD) fibroblasts correlates with the fibroblast-induced downregulation of DMD myoblast growth: an in vitro analysis.* J Cell Physiol, 2000. 185(1): p. 143-53.

80. Chakravarthy, M. V., et al., *Insulin-like growth factor-I extends in vitro replicative life span of skeletal muscle satellite cells by enhancing G1/S cell cycle progression via the activation of phosphatidylinositol 3'-kinase/Akt signaling pathway.* J Biol Chem, 2000. 275(46): p. 35942-52.

81. Chakravarthy, M. V., B. S. Davis, and F. W. Booth, *IGF-I restores satellite cell proliferative potential in immobilized old skeletal muscle.* J Appl Physiol (1985), 2000. 89(4): p. 1365-79.

82. Mourkioti, F., et al., *Targeted ablation of IKK2 improves skeletal muscle strength, maintains mass, and promotes regeneration.* J Clin Invest, 2006. 116(11): p. 2945-54.

83. Christov, C., et al., *Muscle satellite cells and endothelial cells: close neighbors and privileged partners.* Mol Biol Cell, 2007. 18(4): p. 1397-409.

84. Horie, M., et al., *Enhancement of satellite cell differentiation and functional recovery in injured skeletal muscle by hyperbaric oxygen treatment.* J Appl Physiol (1985), 2014. 116(2): p. 149-55.

85. Chaillou, T. and J. T. Lanner, *Regulation of myogenesis and skeletal muscle regeneration: effects of oxygen levels on satellite cell activity.* FASEB J, 2016. 30(12): p. 3929-3941.

86. Oyaizu, T., et al., *Hyperbaric oxygen reduces inflammation, oxygenates injured muscle, and regenerates skeletal muscle via macrophage and satellite cell activation.* Sci Rep, 2018. 8(1): p. 1288.

87. Watt, J., *Surgical applications of hyperbaric oxygen therapy in the Royal Navy.* Proc R Soc Med, 1971. 64(9): p. 877-81.

88. Welch, H. G., et al., *Effects of hyperoxia on leg blood flow and metabolism during exercise.* J Appl Physiol Respir Environ Exerc Physiol, 1977. 42(3): p. 385-90.

89. Haapaniemi, T., et al., *Hyperbaric oxygen treatment attenuates glutathione depletion and improves metabolic restitution in postischemic skeletal muscle.* Free Radic Res, 1995. 23(2): p. 91-101.

90. Gregorevic, P., G. S. Lynch, and D. A. Williams, *Hyperbaric oxygen improves contractile function of regenerating rat skeletal muscle after myotoxic injury.* J Appl Physiol (1985), 2000. 89(4): p. 1477-82.

91. Kaynar, A., et al., *Effects of hyperbaric oxygen therapy on biochemical and histological parameters of muscle groups in proximity to the distracted rat tibia.* Int J Oral Maxillofac Surg, 2014. 43(12): p. 1514-21.

92. Fujita, N., et al., *Effects of hyperbaric oxygen at 1.25 atmospheres absolute with normal air on macrophage number and infiltration during rat skeletal muscle regeneration.* PLoS One, 2014. 9(12): p. e115685.

93. Koca, K., et al., *Effect of hyperbaric oxygen and ozone preconditioning on oxidative/nitrosative stress induced by tourniquet ischemia/reperfusion in rat skeletal muscle.* Acta Orthop Traumatol Turc, 2010. 44(6): p. 476-83.

94. Seyam, O., et al., *Clinical utility of ozone therapy for musculoskeletal disorders.* Med Gas Res, 2018. 8(3): p. 103-110.

95. Xiao, W., et al., *Ozone oil promotes wound healing by increasing the migration of fibroblasts via PI3K/Akt/mTOR signaling pathway.* Biosci Rep, 2017. 37(6).

96. Ozkan, H., et al., *Evaluation and comparison of the effect of hypothermia and ozone on ischemia-reperfusion injury of skeletal muscle in rats.* J Surg Res, 2015. 196(2): p. 313-9.

97. Zhang, M. L., et al., *Effects of therapy using the Celacade system on structural and functional cardiac remodelling in rats following myocardial infarction.* Can J Cardiol, 2009. 25(7): p. e241-7.

98. Clavo, B., et al., *Effect of ozone therapy on muscle oxygenation.* J Altern Complement Med, 2003. 9(2): p. 251-6.

99. Verma, S. K., et al., *Interleukin-10 Inhibits Bone Marrow Fibroblast Progenitor Cell-Mediated Cardiac Fibrosis in Pressure-Overloaded Myocardium.* Circulation, 2017. 136(10): p. 940-953.

100. Meng, X., et al., *Transplantation of mesenchymal stem cells overexpressing IL10 attenuates cardiac impairments in rats with myocardial infarction.* J Cell Physiol, 2018. 233(1): p. 587-595.

Although the present disclosure and its advantages have been described in detail, it should be understood that various changes, substitutions and alterations can be made herein without departing from the spirit and scope of the design as defined by the appended claims. Moreover, the scope of the present application is not intended to be limited to the particular embodiments of the process, machine, manufacture, composition of matter, means, methods and steps described in the specification. As one of ordinary skill in the art will readily appreciate from the present disclosure, processes, machines, manufacture, compositions of matter, means, methods, or steps, presently existing or later to be developed that perform substantially the same function or achieve substantially the same result as the corresponding embodiments described herein may be utilized according to the present disclosure. Accordingly, the appended claims are intended to include within their scope such processes, machines, manufacture, compositions of matter, means, methods, or steps.

What is claimed is:

1. A method of treating a muscular dystrophy in an individual, comprising the step of administering to the individual an effective amount of a composition comprising an adherent population of fibroblast cells or exosomes therefrom, wherein the fibroblast cells express one or more of GDF3; Stella; Rex-1, and CD117.

2. The method of claim 1, wherein the administering results in improvement in muscle function, inhibition of deterioration of muscle function, or a combination thereof.

3. The method of claim 1, wherein the fibroblast cells are derived from tissue selected from the group consisting of the placenta, cord blood, Wharton's Jelly, menstrual blood, endometrium, skin, omentum, amniotic fluid, adipose tissue, bone marrow, umbilical cord tissue, peripheral blood, hair follicle, and a mixture thereof.

4. The method of claim 1, wherein said muscular dystrophy is selected from the group of muscular dystrophies consisting of Duchenne, Becker, limb girdle, congenital, facioscapulohumeral, myotonic, oculopharyngeal, distal, and Emery-Dreifuss dystrophies.

5. The method of claim 1, wherein said population is enriched for cells comprising expression of CXCR-4.

6. The method of claim 1, wherein said fibroblast cells comprise a population of fibroblasts in which >90% of the cells are CD90-positive and/or CD105-positive and in which <5% are CD14-positive, CD34-positive, and/or CD45-positive.

7. The method of claim 1, wherein said fibroblast cells express one or more markers selected from the group consisting of STRO-1, CD105, CD54, CD106, HLA-1 markers, vimentin, ASMA, collagen-1, fibronectin, LFA-3, ICAM-1, PECAM-1, P-selectin, L-selectin, CD49b/CD29, CD49c/CD29, CD49d/CD29, CD61, CD18, CD29, thrombomodulin, telomerase, CD1O, CD13, STRO-2, VCAM-1, CD146, THY-1, and a combination thereof.

8. The method of claim 1, wherein said fibroblast cells are allogeneic, autologous, or xenogenic with respect to the individual.

9. The method of claim 1, wherein said fibroblast cells are matched by mixed lymphocyte reaction matching.

10. The method of claim 1, wherein said fibroblast cells are derived from the skin.

11. The method of claim 10, wherein said fibroblast cells are human skin-derived adherent cells that produce a cytokine selected from the group consisting of a) FGF-1; b) FGF-2; c) HGF; d) interleukin-1 receptor antagonist; and e) a combination thereof.

12. The method of claim 1, wherein said fibroblast cells produce a factor selected from the group consisting of a) arginase; b) indoleamine 2,3 deoxygenase; c) interleukin-10; d) interleukin-35; and e) a combination thereof.

13. The method of claim 1, wherein said fibroblast cells express hTERT, Oct-4 or both.

14. The method of claim 1, wherein the fibroblast cells do not express a STR0-1 marker.

15. The method of claim 1, wherein the fibroblast cells have an ability to undergo cell division in less than 36 hours in a growth medium.

16. The method of claim 1, wherein said fibroblast cells express a STR0-1 marker.

17. The method of claim 1, wherein the fibroblast cells have an ability to proliferate at a rate of 0.9-1.2 doublings per 36 hours in a growth medium.

18. The method of claim 1, wherein said cell produces exosomes capable of inducing a 50% higher proliferation rate in human umbilical cord endothelial cells when cultured with the exosomes at a concentration of 100 exosomes per cell compared to human umbilical cord endothelial cells that have not been cultured with the exosomes.

19. The method of claim 1, wherein the cells are administered locally or systemically.

20. The method of claim 1, wherein said cells are administered intramuscularly, intravenously, or a combination thereof.

21. A method of treating a muscular dystrophy in an individual, comprising the step of administering to the individual an effective amount of a composition comprising an adherent population of fibroblast cells or exosomes therefrom, wherein said population is enriched for cells comprising expression of CXCR-4.

22. A method of treating a muscular dystrophy in an individual, comprising the step of administering to the individual an effective amount of a composition comprising an adherent population of fibroblast cells or exosomes therefrom, wherein said fibroblast cells are matched by mixed lymphocyte reaction matching.

23. A method of treating a muscular dystrophy in an individual, comprising the step of administering to the individual an effective amount of a composition comprising an adherent population of fibroblast cells or exosomes therefrom, wherein said cell produces exosomes capable of inducing a 50% higher proliferation rate in human umbilical cord endothelial cells when cultured with the exosomes at a concentration of 100 exosomes per cell compared to human umbilical cord endothelial cells that have not been cultured with the exosomes.

* * * * *